United States Patent
Randolph et al.

(10) Patent No.: US 9,555,215 B2
(45) Date of Patent: *Jan. 31, 2017

(54) TREATMENT FLUID DELIVERY METHOD, AND TURBULATOR FOR PROMOTING UPTAKE OF A TREATMENT AGENT

(71) Applicant: Cook Medical Technologies LLC, Bloomington, IN (US)

(72) Inventors: James R. Randolph, Bloomington, IN (US); Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/938,906

(22) Filed: Nov. 12, 2015

(65) Prior Publication Data

US 2016/0058972 A1    Mar. 3, 2016

Related U.S. Application Data

(63) Continuation of application No. 14/187,748, filed on Feb. 24, 2014, now Pat. No. 9,308,347, which is a
(Continued)

(51) Int. Cl.
*A61M 25/00* (2006.01)
*A61M 25/01* (2006.01)
*A61B 17/22* (2006.01)

(52) U.S. Cl.
CPC .......... *A61M 25/0023* (2013.01); *A61B 17/22* (2013.01); *A61M 25/0021* (2013.01);
(Continued)

(58) Field of Classification Search
CPC ............. A61M 2025/0057; A61M 2025/0063; A61M 2025/0073; A61M 25/0023; A61M 25/0074
See application file for complete search history.

(56) References Cited

U.S. PATENT DOCUMENTS 4,706,671 A   11/1987   Weinrib
4,798,598 A   1/1989   Bonello et al.
(Continued)

FOREIGN PATENT DOCUMENTS

EP   0963764 A1   12/1999
EP   1013301 A1   6/2000
(Continued)

*Primary Examiner* — Deanna K Hal
(74) *Attorney, Agent, or Firm* — Liell & McNeil

(57) ABSTRACT

A turbulator for promoting mixing of fluids passing through a body lumen includes an elongate flow perturbing component and an elongate shape controlling component freely slidable within the flow perturbing component. The turbulator is adjustable from a low profile, lumen access configuration to a deployed configuration via sliding the shape controlling component within the flow perturbing component. Adjusting the turbulator within a body lumen of a patient induces turbulence within a flow of fluid passing through the body lumen to increase mixing of a treatment fluid with the body fluid by way of the induced turbulence.

8 Claims, 6 Drawing Sheets

Related U.S. Application Data continuation of application No. 13/301,380, filed on May 5, 2011, now Pat. No. 8,696,646.

(60) Provisional application No. 61/331,546, filed on May 5, 2010, provisional application No. 61/391,122, filed on Oct. 8, 2010.

(52) U.S. Cl.
CPC .... *A61M 25/0043* (2013.01); *A61M 25/0067* (2013.01); *A61M 25/0068* (2013.01); *A61M 25/0102* (2013.01); *A61M 25/007* (2013.01); *A61M 25/0069* (2013.01); *A61M 2025/0057* (2013.01); *A61M 2025/0063* (2013.01); *A61M 2025/0073* (2013.01)

(56) References Cited

U.S. PATENT DOCUMENTS

| | | |
|---|---|---|
| 4,917,102 A | 4/1990 | Miller et al. |
| 4,994,069 A | 2/1991 | Ritchart et al. |
| 5,184,627 A | 2/1993 | de Toledo |
| 5,203,772 A | 4/1993 | Hammerslag et al. |
| 5,211,636 A | 5/1993 | Mische |
| 5,217,484 A | 6/1993 | Marks |
| 5,228,453 A | 7/1993 | Sepetka |
| 5,554,114 A | 9/1996 | Wallace et al. |
| 5,573,520 A | 11/1996 | Schwartz et al. |
| 5,669,881 A | 9/1997 | Dunshee |
| 5,709,874 A | 1/1998 | Hanson et al. |
| 5,733,294 A | 3/1998 | Forber et al. |
| 5,797,953 A | 8/1998 | Tekulve |
| 6,074,378 A | 6/2000 | Mouri et al. |
| 6,107,004 A | 8/2000 | Donadio, III |
| 6,117,157 A | 9/2000 | Tekulve |
| 6,277,139 B1 | 8/2001 | Levinson et al. |
| 6,350,253 B1 | 2/2002 | Deniega et al. |
| 6,391,018 B1 | 5/2002 | Tanaka et al. |
| 6,402,736 B1 | 6/2002 | Brown et al. |
| 6,551,340 B1 | 4/2003 | Konya et al. |
| 6,562,058 B2 | 5/2003 | Seguin et al. |
| 6,706,055 B2 | 3/2004 | Douk et al. |
| 6,790,218 B2 | 9/2004 | Jayaraman |
| 6,911,036 B2 | 6/2005 | Douk et al. |
| 6,960,222 B2 | 11/2005 | Vo et al. |
| 7,249,604 B1 | 7/2007 | Mohanraj |
| 7,354,445 B2 | 4/2008 | Nicholson et al. |
| 7,371,248 B2 | 5/2008 | Dapolito et al. |
| 8,696,646 B2 * | 4/2014 | Randolph ......... A61M 25/0021 604/525 |
| 2003/0139751 A1 | 7/2003 | Evans et al. |
| 2007/0073332 A1 | 3/2007 | Miller et al. |
| 2008/0103522 A1 | 5/2008 | Steingisser et al. |

FOREIGN PATENT DOCUMENTS

| | | |
|---|---|---|
| WO | 98/35717 | 8/1998 |
| WO | 03/033050 A1 | 4/2003 |

\* cited by examiner

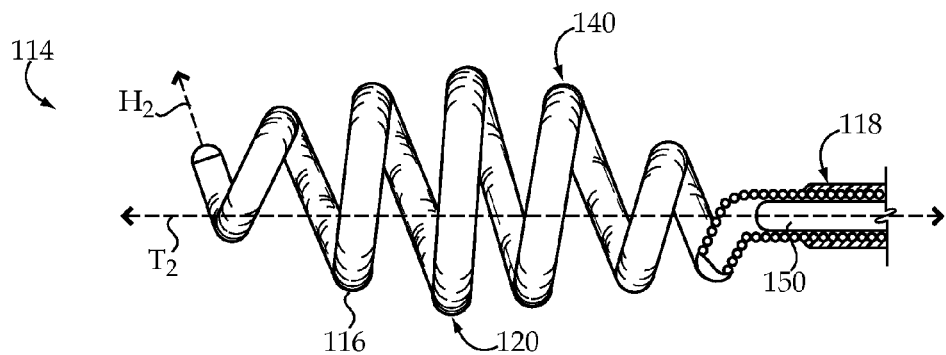
Figure 4
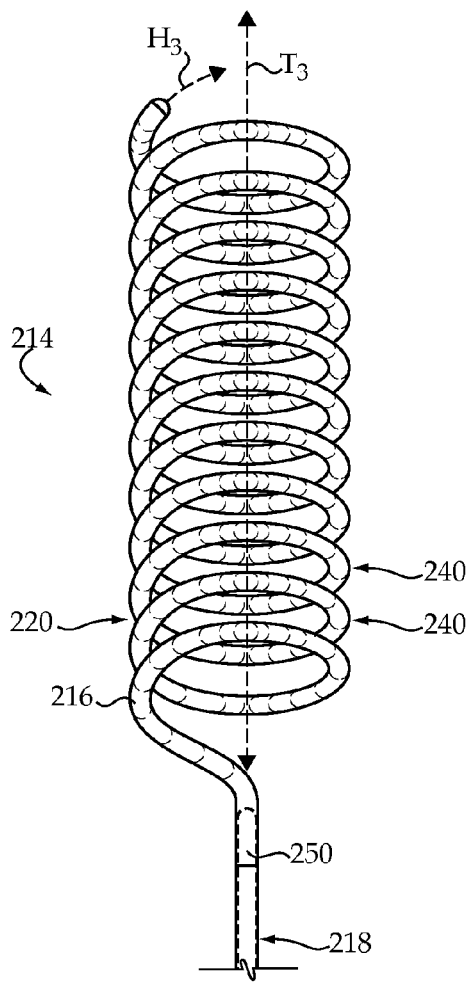
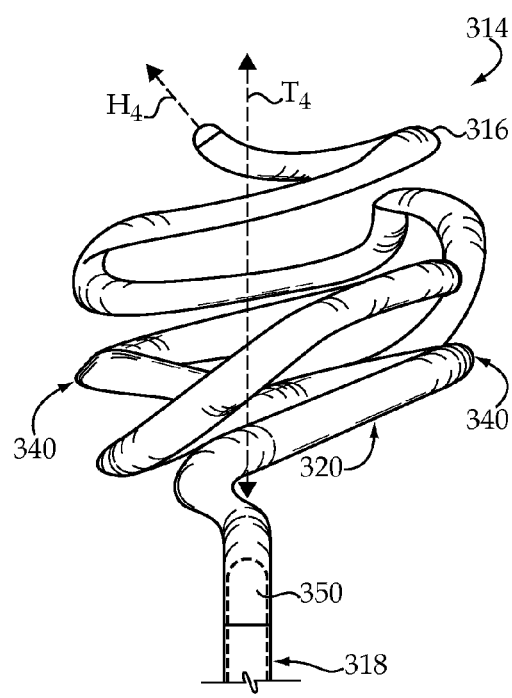
Figure 5  Figure 6

TREATMENT FLUID DELIVERY METHOD, AND TURBULATOR FOR PROMOTING UPTAKE OF A TREATMENT AGENT

TECHNICAL FIELD

The present disclosure relates generally to methods and mechanisms for intraluminal treatment of a patient, and relates more particularly to promoting mixing of a treatment fluid with a body fluid passing through a body lumen of a patient to a downstream treatment site.

BACKGROUND

A wide variety of medical procedures involve the supplying of a treatment fluid into a body lumen of a patient. Peripheral intervention techniques in the human cardiovascular system represent one class of medical procedures where supplying of a treatment fluid is well known for a variety of purposes. For instance, thrombolytic agents are commonly delivered by way of infusion into a vein or artery for the purpose of breaking up and/or dissolving clot material. Another peripheral intervention procedure involves supplying a chemotherapeutic agent which may be carried by blood flow to a treatment site of interest such as a tumor. Peripheral intervention commonly entails percutaneous access to a patient's cardiovascular system. A great many different devices and techniques have been developed over the years for percutaneously accessing treatment sites, and supplying treatment fluids such as the thrombolytic and chemotherapeutic agents mentioned above. Some of these strategies have met with great success in certain treatment contexts, but improvements could be made in others.

Many body tissues are relatively insensitive to the effects of certain treatment agents such as dyes, saline, and others. Other treatment agents may be relatively toxic regardless of tissue type. Such toxicity is not entirely unintended, as in the case of chemotherapeutic agents. Chemotherapeutics are typically designed to kill tumor cells, but can often also damage healthy tissue. While certain thrombolytic agents might not necessarily be considered "toxic," they can have deleterious effects on various parts of the body such as by inducing bleeding. The desire to avoid overuse of certain treatment agents, and avoid their administration outside of target locations, will thus be readily apparent. Such overuse or extraneous administration, however, remains relatively common due to at least in part to difficulty in accessing certain parts of the body, difficulty in controlling flow of treatment fluids in vivo, and incomplete uptake of treatment agents by targeted tissues.

SUMMARY OF THE DISCLOSURE

In one aspect, a method of delivering a treatment fluid to a treatment site within a body lumen of a patient includes, advancing a turbulator including, a shaped controlling component having a dominant shape memory property and a flow perturbing component having a subordinate shaped memory property, through a body lumen. The method further includes adjusting the flow perturbing component from a lumen access shape defined by the dominant shape memory property to an expanded shape defined by the subordinate shape memory property, to increase turbulence in the flow of a body fluid through the body lumen. The method still further includes introducing the treatment fluid into the body lumen such that the treatment fluid and the body fluid are mixed by the increased turbulence while flowing to the treatment site.

In another aspect, a turbulator for promoting mixing of fluids passing through a body lumen in a patient includes an elongate flow perturbing component having a nonporous proximal segment and a porous distal segment, the porous distal segment having a subordinate shape memory property and including an exposed wire coil with a fixed primary shape, a fixed secondary shape, and a mutable tertiary shape. The turbulator further includes an elongate shape controlling component freely slidable within the flow perturbing component between a distally advanced location, and a retracted location. The elongate shape controlling component including a rigid proximal segment having a dominant shape memory property, and a non-rigid distal segment. The turbulator is adjustable from a low profile, lumen access configuration at which the dominant shape memory property defines the mutable tertiary shape, to an expanded profile, deployed configuration at which the subordinate shape memory property defines the mutable tertiary shape, at least in part by sliding the shape controlling component from the distally advanced location to the retracted location.

In still another aspect, a method for promoting uptake of a treatment agent during performing an intraluminal procedure on a patient includes, introducing a treatment fluid containing the treatment agent into a body lumen of the patient having a body fluid flowing therethrough, and increasing mixing of the treatment fluid with the body fluid via adjusting an elongate wire turbulator from a lower turbulence inducing shape to a higher turbulence inducing shape within the body lumen. The method further includes perfusing a body tissue of the patient located at a downstream treatment site with the mixed treatment fluid and body fluid.

BRIEF DESCRIPTION OF THE DRAWINGS

FIG. 4 is a partially sectioned side diagrammatic view of a turbulator in a deployed configuration, according to another embodiment;

FIG. 5 is a side diagrammatic view of a turbulator in a deployed configuration, according to yet another embodiment;

FIG. 6 is a side diagrammatic view of a turbulator in a deployed configuration, according to yet another embodiment;

DETAILED DESCRIPTION

Figure 1:
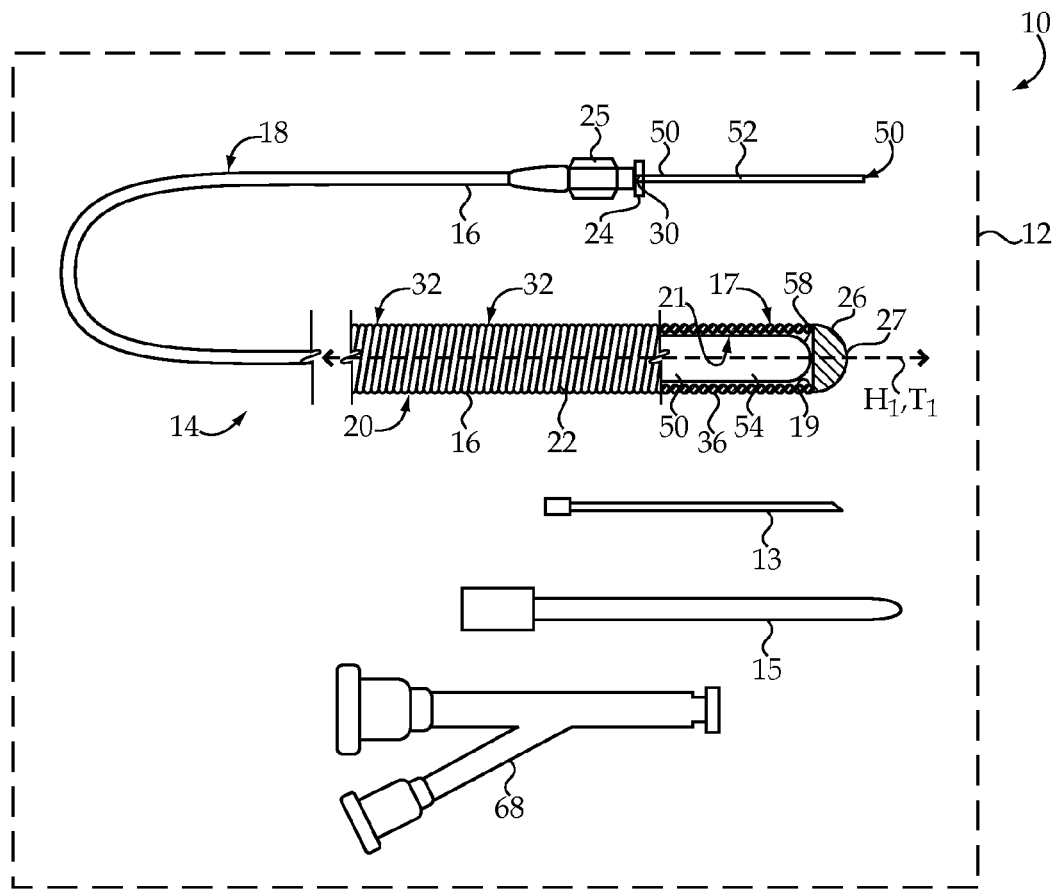
FIG. 1 is a partially sectioned side diagrammatic view of a packaged intraluminal treatment system, according to one embodiment.

Referring to FIG. 1, there is shown an intraluminal treatment system 10 according to one embodiment. System 10 may include a plurality of different components positioned within a sterile package 12, and being configured for use in performing intraluminal treatment procedures as further described herein. Sterile package 12 may include a sealed, peel-open pouch in one embodiment. System 10 may include a turbulator 14 for promoting mixing of fluids passing through a body lumen in a patient, a piercing needle 13, an introducer sheath 15 and an adapter such as a Y-fitting 68, sealed within package 12. Additional components such as a conventional wire guide, and a microcatheter might also be included. As will be further apparent from the following description, system 10 may be uniquely adapted for use in certain procedures in which improved mixing of treatment fluids with body fluids is desired over what can typically be achieved using conventional systems.

Turbulator 14 may include an elongate flow perturbing component 16 having a nonporous proximal segment 18, and a porous distal segment 20. Component 16 may include a proximal end 24 which includes a fitting or manifold 25, and a distal end 26 having a distal tip 27. Tip 27 may include a rounded, atraumatic shape. Distal segment 20 may include an exposed wire coil 22 having a fixed primary shape, a fixed secondary shape, and a mutable tertiary shape. Distal segment 20 may further include a subordinate shape memory property, the significance of which will be further apparent from the following description.

Turbulator 14 may further include an elongate shape controlling component 50 freely slidable within flow perturbing component 16 between a distally advanced location, approximately as shown in FIG. 1, and a retracted location. Elongate shape controlling component 50 may include a rigid proximal segment 52 having a dominant shape memory property, and a non-rigid distal segment 54. In FIG. 1, a proximal end 56 of component 50 is shown positioned outside of component 16, and a distal end 58 of component 50 is shown abutting tip 27, at the distally advanced location mentioned above. Turbulator 14 may be adjusted from a low profile, lumen access configuration at which the dominant shape memory property defines the mutable tertiary shape of exposed wire coil 22, to an expanded profile, deployed configuration at which the subordinate shape memory property defines the mutable tertiary shape, via sliding component 50 from the distally advanced location to a retracted location.

Figure 2:
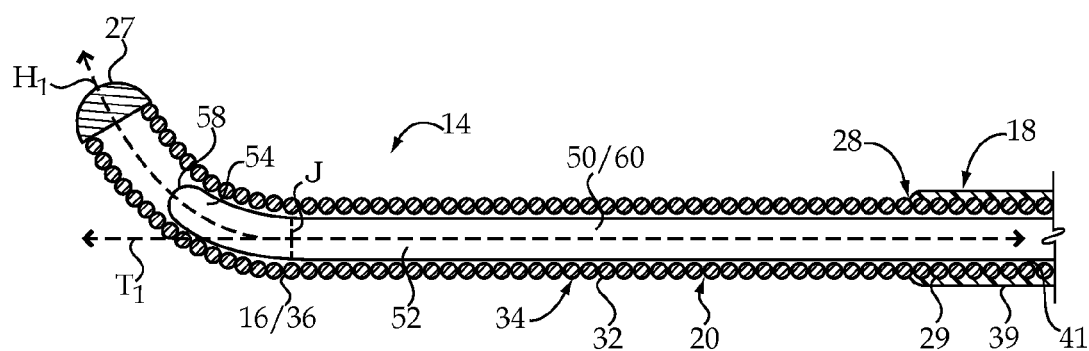
FIG. 2 is a sectioned side diagrammatic view of a portion of a turbulator, according to one embodiment.

To this end, component 16 may include an outer surface 17, and an inner surface 21 defining a control lumen 19 receiving component 50 coaxially and slidably therein. Referring also to FIG. 2, component 16 may further include a tubular fluid supply conduit 29 extending between fluid inlet 30, and at least one fluid outlet 32 located in distal segment 20. In one embodiment, supply conduit 29 may include a nonporous sheath 39 extending from fluid inlet 30 to a proximal end 28 of exposed wire coil 22. Sheath 39 may include an external sheath, comprised of a suitable material such as a fluoropolymer, heat shrunk about component 16 or attached by another suitable means. Control lumen 19 may continuously transition into a fluid passage 41 defined by fluid supply conduit 29.

In the embodiment shown, component 16 includes a helical wire 36 extending through each of proximal segment 18 and distal segment 20. In one embodiment, helical wire 36 may be formed into a constant pitch uniform diameter helical shape. Helical wire 36 includes exposed wire coil 22 within distal segment 20, and defines a longitudinal helix axis $H_1$. Shape controlling component 50 may include a non-helical wire 60. As mentioned above, one or more fluid outlets 32 may be formed in distal segment 20. In one embodiment, the one or more fluid outlets 32 may be defined by a plurality of wire turns 34 of exposed wire coil 22. Adjacent wire turns 34 may normally abut one another, but be slightly squeezed apart by a pressure of fluid passed through fluid supply conduit 29 and control lumen 19, as further described herein. In other embodiments, helical wire 36 may be formed into a helical shape having a varying pitch, or non-uniform in diameter, or even having slots or the like formed therein which define fluid outlets 32.

As mentioned above, FIG. 1 illustrates component 50 at a distally advanced location within component 16, at which distal tip 58 abuts or is adjacent to distal tip 27. When component 50 is positioned at the distally advanced location within component 16, approximately as shown in FIG. 1, turbulator 14 may be understood to be in the low profile, lumen access configuration. When component 50 is retracted, turbulator 14 may be understood to be in one of several possible expanded profile, deployed configurations. The low profile configuration facilitates advancing turbulator 14 through a body lumen in a patient during or in preparation for performing an intraluminal treatment procedure, whereas the expanded profile configuration enables inducement of turbulence within the body lumen in a manner further described herein for promoting mixing of fluids within the body lumen.

In FIG. 2, component 50 has been slid in a distal to proximal direction relative to the state shown in FIG. 1, but has not yet been slid far enough to enable the full deployment of turbulator 14, and thus the FIG. 2 illustration may be understood as an intermediate configuration between low profile and fully expanded profile configurations. It may be noted that a shape of component 16 as depicted in FIG. 2 has changed from a shape depicted in FIG. 1. It may also be noted that axis $H_1$ and a second longitudinal axis $T_1$ defined by fluid passage 41 have changed from a collinear state shown in FIG. 1, to a partially overlapping but partially divergent state shown in FIG. 2. In the low profile configuration, component 16 may be understood to be radially condensed relative to axis $T_1$. As used herein, the term "radially condensed" means that a radius of a circle having a center within longitudinal axis $T_1$ and a perimeter tangent to a radially outermost point of component 16, e.g. tangent to radially outermost points of outer surface 17, is relatively small. In the configuration shown in FIG. 2, component 16 may be understood to be radially expanded relative to axis $T_1$. "Radially expanded" means that the radius described above is relatively large. The change in shape in component 16 which is evident from comparing FIG. 1 with FIG. 2, and more dramatic changes in shape as further described herein, results at least in part from the differing shape memory properties of component 16 versus component 50 mentioned above.

In one practical implementation strategy, the dominant shape memory property of component 50 may define a shape of distal segment 20 at the distally advanced location of component 50. At a retracted location of component 50 as shown in FIG. 2, distal segment 20 has begun to assume a shape which is defined by the subordinate shape memory property. At progressively more retracted locations of component 50, relatively more of segment 20 may assume a shape defined by the subordinate shape memory property. Another way to understand the relationship between the respective shape memory properties is that the dominant shape memory property may define a shape of any portion of component 16 within which component 50 is presently positioned, subject to certain exceptions described herein.

Portions of component 16 within which component 50 is not presently positioned may have a shape defined by the subordinate shape memory property. In the example embodiments described herein, component 50 includes a rest state which defines a generally linear shape. Thus, when no external deforming force is applied to shape control component 50, it may be expected to assume a generally linear configuration. Portions of component 16 within which component 50 is presently positioned may likewise be expected to assume a generally linear shape in response to the dominant shape memory property.

Component 16 may further be understood to be in a biased state in the low profile configuration, where the dominant shape memory property is at least predominantly responsible for determining its shape. As mentioned above, in the biased state component 16 may have a generally linear shape. Component 16 may also include a rest state, assumed when component 50 has been retracted, which includes a non-linear, or curvilinear, shape. Thus, in the lumen access configuration as depicted in FIG. 1, component 16 may be generally linear to facilitate access or advancing through a body lumen, but may have a non-linear shape in the deployed configuration for purposes which will be apparent from the following description. It will further be understood that the biased state of component 16 may include a state in which helical wire 36 is radially condensed relative to axis $T_1$. It will still further be understood that the rest state of component 16 may include a state in which wire 36 is radially expanded relative to axis $T_1$.

It will be recalled that distal segment 54 of component 50 may be non-rigid relative to proximal segment 52. A dashed line J in FIG. 2 denotes one example location where component 50 transitions from rigid to non-rigid in a proximal to distal direction. Accordingly, in the state depicted in FIG. 2 a shape of distal segment 54 is in fact determined by a shape of component 16. Thus, while proximal segment 52 of component 50 is relatively rigid, and thus includes the dominant shape memory property, distal segment 54 may be relatively soft or floppy, and thus have a different shape memory property than the rest of component 50. This aspect of the present disclosure allows for component 50 to track relatively readily through component 16 during sliding, and in particular during advancing component 50 in a proximal to distal direction to radially condense component 16 as further described herein. Another way to understand this configuration, is that a majority of an axial length of component 50 may have the dominant shape memory property and thus determine a shape of component 16 when positioned therein, but a relatively short portion of component 50 extending proximally from distal end 58 may in fact not include the dominant shape memory property, hence the illustration in FIG. 2 of distal end 58 curving in response to curving of component 16 away from axis $T_1$. A distal-most portion of component 16, adjoining end 26, may also be relatively soft or floppy, compared to the rest of distal segment 20. Thus, distal segment 54 of component 50 might have a shape memory property which is dominant relative to a shape memory property of distal segment 20 near distal end 26, but subordinate to other parts of distal segment 20. On the whole, at least a majority of distal segment 20 of component 16 will have a shape memory property characterized as "subordinate," while at least a majority of component 50 will have a shape memory property characterized as "dominant." It should be understood in any event that tertiary shape control according to the present disclosure will typically occur via the tendency of component 50 to straighten component 16 by contacting inner surface 21, i.e. applying forces in a vector direction transverse to axis $H_1$. This contrasts with strategies in which a stiff core wire is used to straighten an outer sheath via axial forces, although such strategies may still fall within the scope of the present disclosure.

Figure 3:
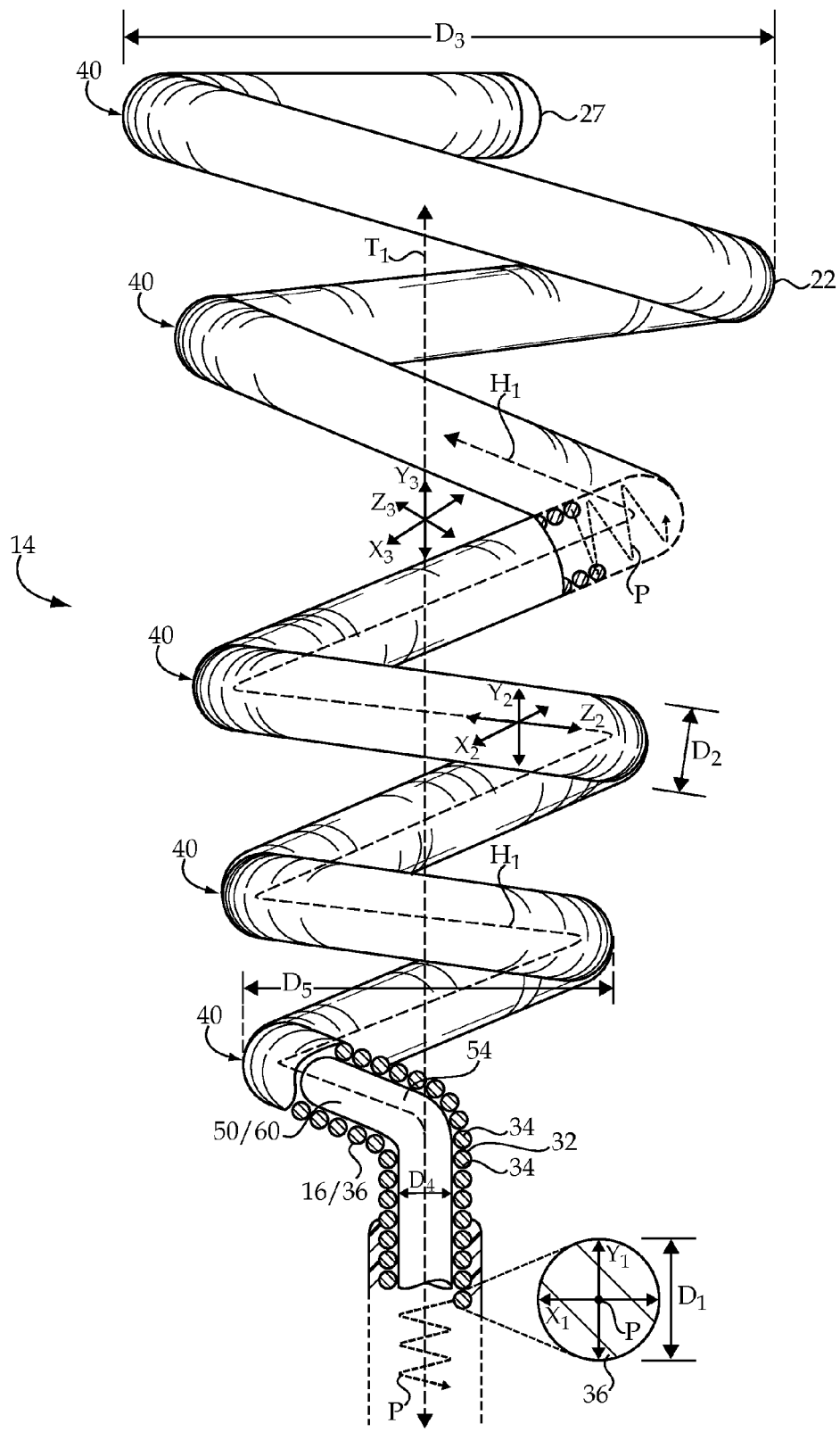
FIG. 3 is a partially sectioned side diagrammatic view of a turbulator in a deployed configuration, including a detailed enlargement, according to one embodiment.

Referring also now to FIG. 3, there is shown turbulator 14 where component 50 has been further refracted within component 16 relative to the state shown in FIG. 2. A relatively greater axial length of component 16 now assumes a shape defined by the subordinate shape memory property. As mentioned above, component 16 may include wire turns 34. Wire turns 34 correspond to individual turns of helical wire body 36, about helix axis $H_1$. Component 16 may also include a plurality of body turns 40 about longitudinal axis $T_1$. Wire turns 32 may thus be understood to define a minor curving shape about axis $T_1$, which may include a spiral shape, whereas body turns 40 may be understood to define a major curving shape about axis $T_1$, which may also include a spiral shape. In one embodiment, body turns 40 may be non-uniform in size and/or shape. To this end, body turns 40 may include each of a small radius turn, for example the lowermost turn in FIG. 3, and one or more large radius turns, each of the small and large radius turns being circumferential of axis $T_1$.

As discussed above, the shape of turbulator 14, and in particular flow perturbing component 16, which may be varied by sliding component 50 therein may be understood as a mutable tertiary shape, and component 16 may also be understood to include a fixed primary shape, and a fixed secondary shape. The terms "primary shape," "secondary shape," and "tertiary shape," are used herein in a manner analogous to similar terms used to describe hierarchical shapes of certain biomolecules such as proteins. Thus, the primary shape of component 16 may be understood as a low level shape, the secondary shape may be understood as a middle level shape, and the tertiary shape may be understood as a high level shape. Stated yet another way, the fixed primary shape may be a basic shape of helical wire 36 from which component 16 is formed, the fixed secondary shape may be understood as a shape into which wire 36 is wound, and the mutable tertiary shape may be understood as a shape which the wound wire 36 assumes under the varying conditions described herein.

FIG. 3 illustrates still further geometric attributes of turbulator 14 associated with the primary, secondary, and tertiary shapes. Helical wire 36 may further define a primary axis P which is internal to helical wire 36. Primary axis P may include a longitudinal center axis of helical wire 36. The fixed primary shape of component 16 may include a cross sectional shape of helical wire 36 in two dimensions defined by primary axis P. In the illustrated embodiment, the fixed primary shape may include a rounded cross-sectional shape such as a circular shape in the plane of the page of FIG. 3. The two dimensions $Y_1$ and $X_1$ defined by primary axis P are perpendicular to one another and each intersect primary axis P, and are oriented perpendicular to primary axis P. A circular fixed primary shape represents one practical implementation strategy, however, in other embodiments a non-circular shape such as an oval shape or a polygonal shape might be used, for example. Helical wire 36 may further define a secondary axis which includes axis $H_1$. Axis $H_1$ may be external to helical wire 36 and internal to wire turns 34. The secondary shape may include a fixed secondary shape in three dimensions defined by axis $H_1$, such as the minor curving shape of helical wire 36 mentioned above. In FIG. 3, the three dimensions defined by secondary axis $H_1$ are shown as dimensions $X_2$, $Y_2$ and $Z_2$, and the fixed secondary shape includes a helical shape with axis $H_1$ comprising a helix center axis overlapping with dimension $Z_2$.

Helical wire 36 may still further define a tertiary axis, which in FIG. 3 is collinear with axis $T_1$ and commonly labeled therewith. The tertiary axis may include a geometric center axis of component 16. Thus, the tertiary axis may be defined by geometric center points of the tertiary shape of component 16 proceeding in a proximal to distal direction. Although the tertiary axis may intersect wire 36 and wire turns 34 at certain locations, at least a majority of the tertiary axis may be external to wire 36 and external to wire turns 34 when component 16 is in the rest state and turbulator 14 is in the expanded profile configuration approximately as shown in FIG. 3. Referring back to FIG. 1, it may be appreciated that the tertiary axis $T_1$ may be external to wire 36 and internal to wire turns 34 when component 16 is in the biased state and turbulator 14 is in the low profile configuration.

The tertiary shape of component 16 may include a shape of wire 36 in three dimensions defined by the tertiary axis $T_1$, and labeled $X_3$, $Y_3$, and $Z_3$ in FIG. 3. The mutable tertiary shape may further include a major curving shape such as a spiral or helical shape in dimensions $X_3$, $Y_3$ and $Z_3$. The tertiary shape may further include a lower turbulence inducing shape in the low profile, lumen access configuration, and a higher turbulence inducing shape in the expanded profile, deployed configuration. The higher turbulence inducing shape may include at least one turn about axis $T_1$. The at least one turn may correspond to body turns 40, and in the FIG. 3 embodiment the tertiary shape includes a total of five body turns 40 about axis $T_1$; however, a different number of body turns may be used depending upon the application. As used herein, the term "helical" shape is intended to refer to a type of spiral shape. Thus, the tertiary shape shown in FIG. 3 may be understood as a curving shape, and a spiral shape, but not a helical shape. The tertiary shape shown in FIG. 3 may also be understood as having a distally expanding taper.

Also shown in FIG. 3 are several dimensional attributes of turbulator 14. In particular, a primary dimension $D_1$ corresponding to an outer diameter or wire thickness of wire 36 is shown, and may be equal to between about 2/1000ths inches or 0.05 millimeters, and about 3/10000ths inches or 0.08 millimeters in one embodiment. A secondary dimension $D_2$ corresponding to an outer diameter dimension of a coil or helix into which wire 36 is wound is also shown in FIG. 3, and may be less than about 20/1000ths inches or 0.51 millimeters, and further may be equal to between about 11/1000ths inches or 0.28 millimeters and about 18/1000ths inches or 0.46 millimeters in one embodiment. In one further embodiment, dimension $D_1$ may be equal to about 2/1000ths inches, and dimension $D_2$ may be equal to about 11/1000ths inches. In still another embodiment, dimension $D_1$ may be equal to about 3/1000ths inches and dimension $D_2$ may be equal to between about 15/1000ths inches or 0.38 millimeters and about 18/1000ths inches.

Another dimension $D_3$ is shown in FIG. 5 and corresponds to a mutable outer diameter dimension in a direction perpendicular to and intersecting axis $T_1$, and extending between radially outermost points of distal segment 20 relative to axis $T_1$. Dimension $D_3$ may be equal to about 118/1000ths inches or about 3 millimeters in one embodiment. From a maximum width equal to $D_3$, the tertiary shape depicted in FIG. 3 may taper in a proximal direction to another mutable outer diameter dimension $D_5$ of about 79/1000ths inches or about 2 millimeters, approximately halfway between the body turns 40 indicated first and second from the bottom in FIG. 3. In one further embodiment, $D_3$ may be equal to less than about 20/1000ths inches in the lumen access configuration, and greater than about 20/1000ths inches and less than about 118/1000ths inches in the deployed configuration. Still another dimension $D_4$ is shown in FIG. 3, and represents an outer diameter or wire thickness of wire 50. $D_4$ may be equal to between about 5/1000ths inches or about 0.13 millimeters and about 7/1000ths inches or about 0.18 millimeters, in one embodiment. In one further example embodiment, $D_4$ may be equal to at least about 33%, and may be equal to 40% or greater, of $D_2$.

As used herein, "about" 2 millimeters may be understood as equal to between 1.5 and 2.4 millimeters. "About" 2/1000ths inches may be understood to be between 1.5/1000ths inches and 2.4/1000ths inches, and so on. It should further be appreciated that the mutable dimensions will typically vary depending upon where component 50 is axially positioned within component 16. It may thus be appreciated that a range of length, width, height, shape, etc., of component 42 may be available, and a clinician manipulating turbulator 14 as further described herein may choose to utilize a shape and/or dimensions of component 16 in vivo which need not be specifically determined until the associated procedure is being performed. It may thus be appreciated that certain component shapes and dimensions may have essentially infinite adjustability.

Turning now to FIG. 4, there is shown a turbulator 114 according to another embodiment. Turbulator 114 includes an elongate flow perturbing component 116 having a proximal segment 118 and a distal segment 120 which includes a helical wire. Turbulator 114 may further include an elongate shape controlling component 150 which may include a non-helical wire. Component 114 may include a fixed primary shape, a fixed secondary shape, and a mutable tertiary shape, and is adjustable in a manner similar to that described above in connection with turbulator 14. Turbulator 14 is shown as it might appear in a deployed configuration, in which a secondary axis $H_2$ curves about a tertiary axis $T_2$, for example in a spiral pattern. Turbulator 114 may be similar in many respects to turbulator 14 described above, but rather than a distally expanding taper, component 316 may be configured to assume a roughly diamond tertiary shape, having body turns 140 which are of larger diameter at a middle location, and smaller diameter at distal and proximal locations of segment 120. Thus, the tertiary shape of component 116 may be understood as bidirectionally tapered in an expanded profile, deployed configuration.

Referring to FIG. 5, there is shown a turbulator 214 according to yet another embodiment. Turbulator 214 includes an elongate flow perturbing component 216 having a proximal segment 218 and a distal segment 220 which includes a helical wire. Turbulator 214 may further include an elongate shape controlling component 250 which may include a non-helical wire. Component 214 may include a fixed primary shape, a fixed secondary shape, and a mutable tertiary shape, and is adjustable in a manner similar to that described above in connection with the foregoing embodiments. Turbulator 214 is shown as it might appear in a deployed configuration in which a secondary axis $H_3$ curves about a tertiary axis $T_3$, in a helical pattern. Turbulator 214 may also be similar in many respects to the foregoing embodiments, but rather than a tapering tertiary shape, component 216 may be configured to assume a uniform diameter helical shape having a plurality of uniform diameter body turns 240.

Turning to FIG. 6, there is shown a turbulator 314 according to yet another embodiment, and including an elongate flow perturbing component 316 and an elongate shape controlling component 350. Turbulator 14 is also similar in many respects to the embodiments described above, but includes a complex tertiary shape. Component 316 includes a proximal segment 318 and a distal segment 320 defining a secondary axis $H_4$, and a tertiary axis $T_4$. It may be noted that the tertiary shape of the embodiment of FIG. 6 includes a plurality of body turns 340 about tertiary axis $T_4$.

A variety of materials and manufacturing techniques may be used in constructing turbulators, wire guides, and components thereof in accordance with the present disclosure. Techniques are known whereby wires and wire coils of metallic materials such as stainless steel, Nitinol®, and other metallic materials may be treated to impart a range of shape memory properties, and a wide variety of shapes assumed when the wires and wire coils are in a rest state. A variety of techniques are also known whereby the dominant shape memory property associated with shape controlling components 50, 150, 250, 350 and the subordinate shape memory properties associated with flow perturbing components 16, 116, 216, 316, may be established. For example, components 50, 150, 250, 350 might be formed from a metallic material having a relatively greater stiffness than material from which components 16, 116, 216, 316 may be formed. Processing techniques such as heat treating may be used whereby wire stiffness of the different wires is tailored to achieve a dominant versus subordinate shape memory property, or varying shape memory properties within a single wire such as the different rigidity of segments 52 and 54 in turbulator 14. In still further examples, differing gauge and/or shape of the wire used to manufacture components 50, 150, 250, 350 versus components 16, 116, 216, 316, could impart the desired differing shape memory properties.

INDUSTRIAL APPLICABILITY

Figure 7:
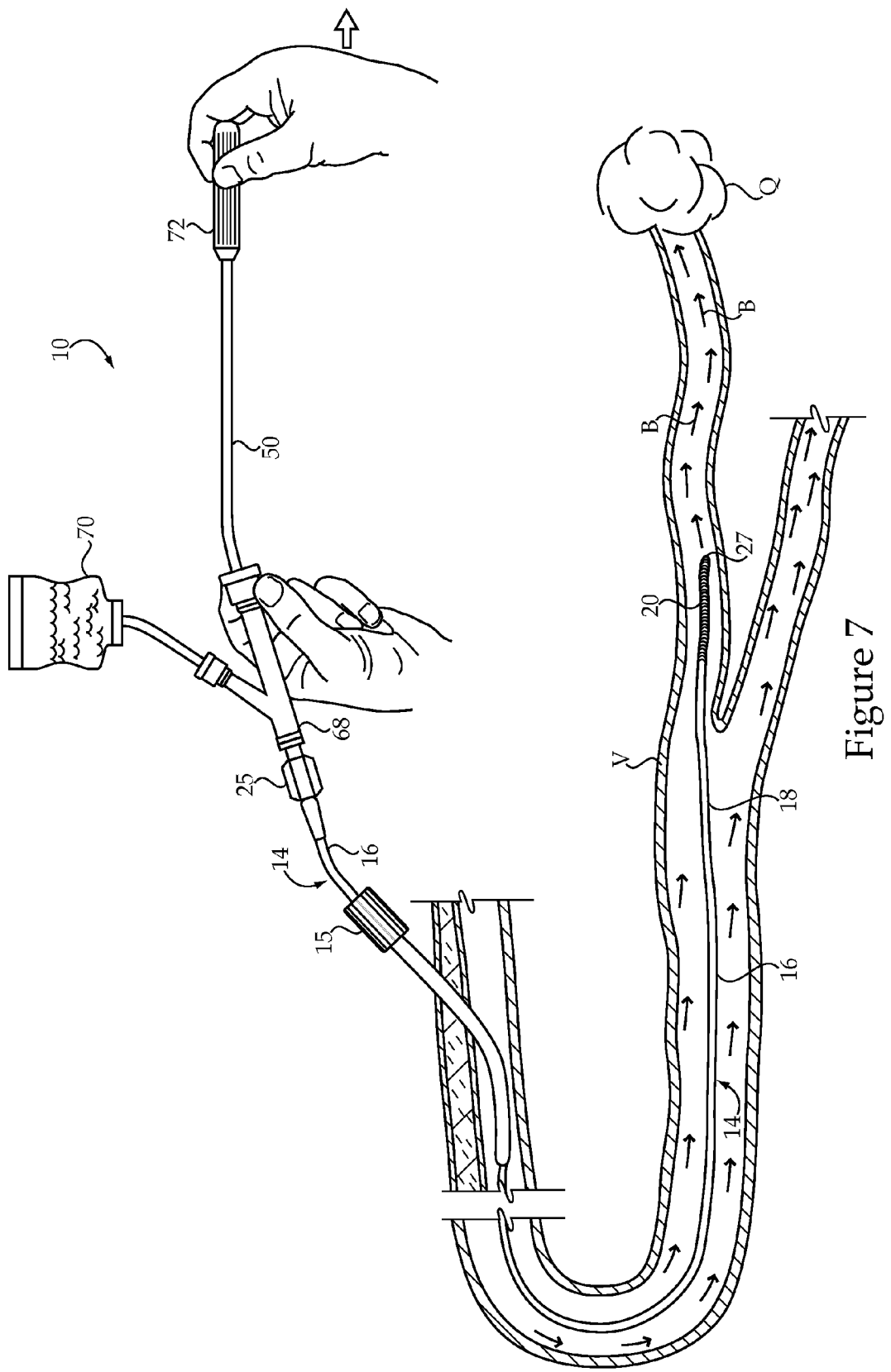
FIG. 7 is a pictorial view of one stage of an intraluminal treatment procedure.

Referring to the drawings generally, but in particular now to FIG. 7, there is shown intraluminal treatment system 10 as it might appear at one stage of a treatment procedure according to the present disclosure. It will be recalled that turbulator 16 may include a fitting or manifold 25 configured to connect with an adapter such as Y-fitting 68, approximately as shown in FIG. 7. A fluid supply 70 is connected with Y-fitting 68 to enable the supplying of a treatment fluid such as a chemotherapeutic agent to a body lumen of a patient, by way of fluid passage 41 and control lumen 19. System 10 is also shown as it might appear having been placed by way of percutaneous access to a patient's cardiovascular system. Access for certain procedures contemplated herein may include femoral or brachial access, for example for treating a kidney tumor, however, the present disclosure is not thereby limited. Introducer 15 passes through the patient's skin, and turbulator 14 extends through the vasculature to a point at which tip 27 is positioned upstream of a treatment site such as a tumor, denoted via reference numeral Q. In FIG. 7, arrows B denote an approximate anterograde direction of blood flow within a vascular lumen V, and it may be noted that blood is flowing downstream past turbulator 14 to treatment site Q. In one embodiment, turbulator 14 may be used as a wire guide which is advanced through vascular lumen V to a desired location upstream of treatment site Q. In other embodiments, turbulator 14 might be placed by way of a placement sheath, or passed through a microcatheter or the like. A conventional wire guide might also be employed to reach a desired location within the vasculature, and then a placement sheath positioned via the conventional wire guide, the wire guide removed, and then turbulator 14 advanced through the vasculature to the desired location. Where additional components such as a conventional wire guide and microcatheter are included in package 12, a clinician could select one of several different options for placement of turbulator 14. Those skilled in the art will thus appreciate that a variety of different placement strategies might be employed, and the present disclosure is not limited to any particular one. Moreover, since turbulator 14 may function as a wire guide, it may be used in procedures different from those described herein.

In FIG. 7, a handle 72 is attached to component 50, and enables a clinician to manipulate turbulator 14 within vascular lumen V. It will also be recalled that component 50 is not attached to component 16, and freely slidable therein to adjust component 16 between a lower turbulence inducing shape and a higher turbulence inducing shape. With turbulator 14 positioned approximately as shown in FIG. 7, component 50 may be slid relative to component 16 between a first location at which the dominant shape memory property of component 50 imparts the low profile, lumen access configuration, and a second location at which the subordinate shape memory property of component 16 imparts the expanded profile, deployed configuration. Sliding component 50 relative to component 16 might take place by pulling component 50 in a distal to proximal direction. Alternatively, or in combination with pulling component 50, component 16 might be pushed in a proximal to distal direction to advance component 16 beyond component 50. One practical implementation strategy includes holding component 16 relatively stationary, and pushing component 16 in the proximal to distal direction. This particular technique is believed to assist a clinician in accurately positioning component 16 at a desired deployment location within vascular lumen V, typically with the assistance of radiography. Regardless of whether pushing, pulling, or a combination is used, component 50 may be repositioned such that its dominant shape memory property no longer defines the tertiary shape of component 16, and instead the tertiary shape is defined by the subordinate shape memory property. In one embodiment, component 50 may be completely removed from the patient when turbulator 14 is deployed.

Figure 8:
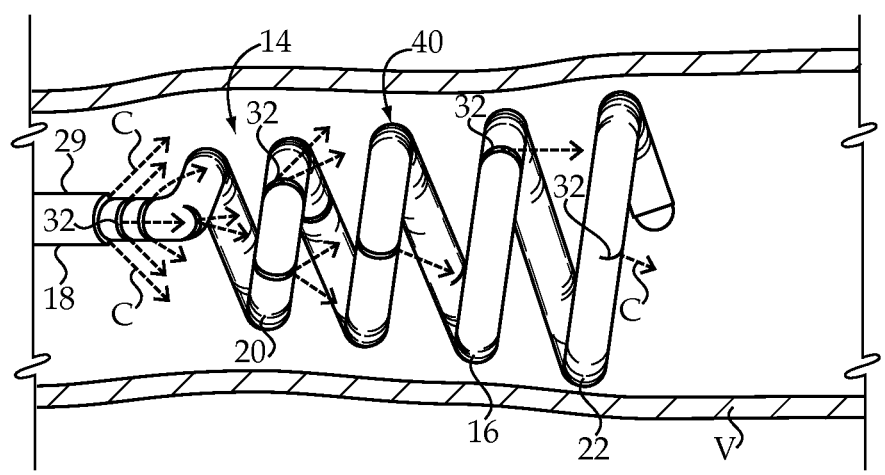
FIG. 8 is a pictorial view of another stage of the intraluminal treatment procedure.

Referring also to FIG. 8, there is shown turbulator 14 as it might appear after component 16 has been adjusted to the expanded profile, deployed configuration. In FIG. 8, a treatment fluid such as a chemotherapeutic agent is being supplied into vascular lumen V by way of fluid supply conduit 29. In particular, the treatment fluid shown via arrows C is being effused into vascular lumen V by way of fluid outlets 32. Treatment fluid flowing from conduit 29 into distal segment 20 may tend to lose pressure as the fluid travels more distally. At least for constant pitch, uniform wire coil embodiments, the loss in pressure may be expected to result in a relatively greater effusion rate and amount in more proximal portions of exposed wire coil 22 versus more distal portions. For this reason, arrows C are shown relatively denser in regions of distal segment 20 adjacent proximal segment 18, and relatively less dense in more distal regions. It should be appreciated, however, that porosity of segment 20 might be tailored to promote uniform or non-uniform effusion of treatment fluid C.

Certain tumors and other areas of undesired tissue within a patient may have a relatively complex vasculature. Numerous small blood vessels may form a fairly chaotic blood supply network within such body tissues. It is believed that this relatively un-ordered vascular structure can render certain tissues such as tumors relatively insensitive to certain treatment techniques, such as treatment with a mixture of treatment fluid and body fluid. For example, where a treatment fluid is supplied by way of perfusion to the vasculature of a tumor, relatively poor mixing of a treatment agent such as a chemotherapeutic agent in the blood can result in certain parts of the tumor receiving an inordinate proportion of the treatment agent, while other parts of the tumor receive little, if any. This phenomenon is believed to be due at least in part to a relatively laminar flow of blood and thus treatment fluid through a vascular lumen upstream of the treatment site. When the blood arrives at the tumor, certain parts of the tumor vasculature may disproportionally receive the chemotherapeutic agent. This potentially reduces the effectiveness of the chemotherapy procedure, or may require excessive quantities of chemotherapeutic agent, or long treatment durations. It has long been recognized that oversupply of treatment fluid to a targeted body tissue can result in excess treatment fluid flowing to downstream body tissue, and having various deleterious affects. The present disclosure enables the promoting of uptake of a treatment agent during performing a procedure on a patient, such that the effectiveness of the treatment agent on target tissue is increased, while supplying of the treatment agent to tissues downstream from the treatment site is reduced. These advantages are made possible by way of perturbing laminar flow to induce turbulence in the flow of body fluid passing distal segment 20. As a result, increased mixing of the treatment fluid and the body fluid is possible in comparison to what might otherwise occur using conventional techniques.

Figure 9:
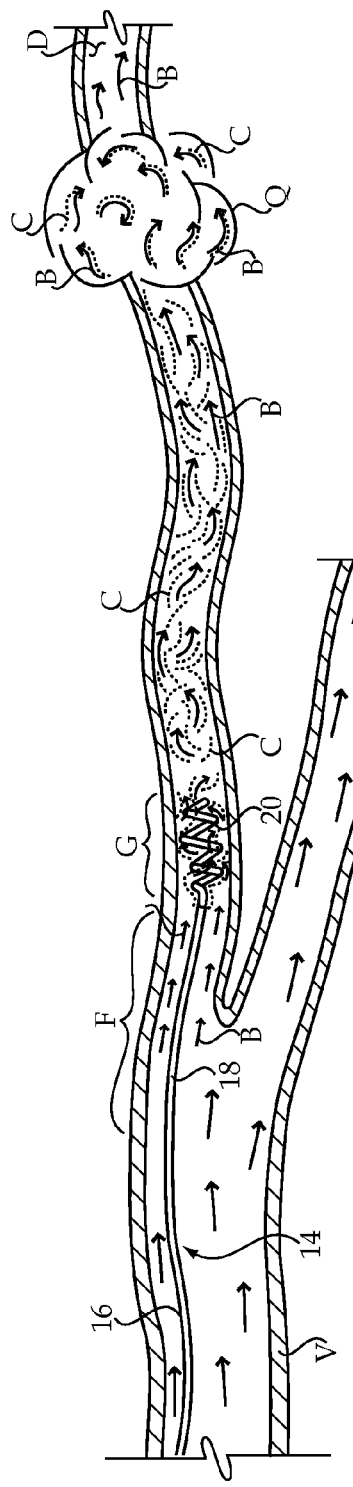
FIG. 9 is a pictorial view of yet another stage of the intraluminal treatment procedure.

It will be recalled that adjusting turbulator 14 from the low profile configuration to the expanded profile configuration adjusts distal segment 20 from a lower turbulence inducing shape, to a higher turbulence inducing shape within a body lumen such as vascular lumen V. In particular, adjusting the mutable tertiary shape of distal segment 20 can increase tortuosity of a fluid flow path through vascular lumen V. Referring now to FIG. 9, it may be noted that a flow of body fluid B upstream of distal segment 20 is relatively uniform and, hence, relatively laminar. This upstream region is denoted as zone F. A second zone G of vascular lumen V is also shown, and corresponds approximately to a portion of lumen V within which distal segment 20 has the higher turbulence inducing shape. It may be noted that the flow of blood and treatment fluid in zone G is relatively non-uniform, and the blood and treatment fluid may flow over, about, and through distal segment 20. Flow of body fluid and treatment fluid may also proceed around distal segment 20, through gaps defined by body turns of distal segment 20 and an inner wall of vascular lumen V. Relatively laminar fluid flow through zone F changes to relatively turbulent flow through zone G, and continuing downstream from zone G. Thus, increased mixing may occur while the body fluid and treatment fluid are passing turbulator 16, and also while continuing to flow downstream thereof. Within treatment site Q, a relatively greater proportion of the vasculature within the treatment site is perfused via mixed treatment agent and blood than what would be expected with a conventional approach. Downstream of treatment site Q, little, if any, treatment agent is evident.

A typical chemotherapeutic treatment such as a treatment of a tumor within a kidney or other organ may be a relatively short procedure, where the treatment fluid is supplied for a time less than thirty minutes. To conclude treatment, a clinician will typically take appropriate steps to cease supplying the treatment fluid, and remove whatever devices from the patient which can be removed. Turbulator 14 may be removed from vascular lumen V after ceasing supplying the treatment agent at least in part by radially condensing distal segment 20, for example by sliding component 50 relative to component 16 back toward the distally advanced location within component 16, or by pushing component 50 in a proximal to distal direction, or by a combination of the two. A sheath or the like may also be used to collapse or otherwise radially condense turbulator 14. Once turbulator 14 has been partially or completely returned to a low profile lumen access configuration, it may be removed from the patient and other appropriate post-procedural activities undertaken.

Figure 10:
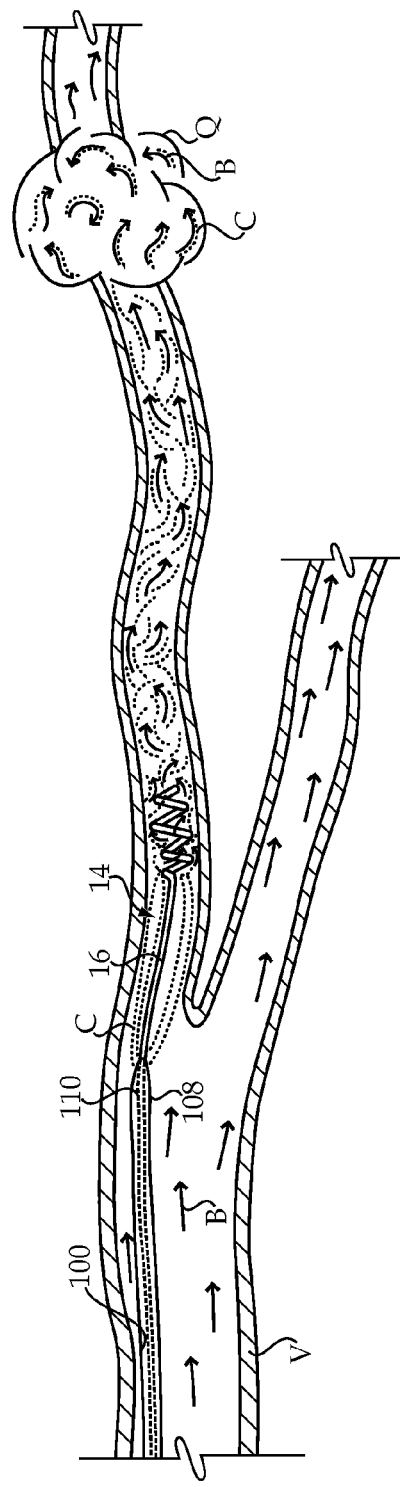
FIG. 10 is a pictorial view of one stage of an intraluminal treatment procedure, according to another embodiment.

Referring now to FIG. 10, there is shown a turbulator 14 similar or identical to the embodiment described above, but used in a different manner. In the procedure depicted in FIG. 10, a microcatheter or the like 100 is positioned within the patient, and defines a longitudinally extending lumen 108 within which turbulator 14 is positioned. By way of lumen 108, or a second lumen, treatment agent may be supplied via one or more ports 110 formed in catheter 100 and fluidly connecting with lumen 108. In the version shown in FIG. 10, treatment agent may be supplied through catheter 100 instead of or in addition to being supplied through turbulator 14, and the overall procedure may otherwise take place in a similar manner.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For example, certain embodiments described herein may be relatively small, well-suited to small vascular lumens. The present disclosure is not limited in this regard, however, and relatively larger turbulator designs are contemplated herein. Thus, the present teachings may be expected to scale up or down. Moreover, a great many tertiary shapes for deployed turbulators beyond those specifically illustrated herein might be used. For instance, a turbulator might be designed such that its flow perturbing component assumes a 2-dimensional coil when deployed, in contrast to the 3-dimensional shapes shown herein. Other aspects, features and advantages will be apparent upon an examination of the attached drawings and appended claims.

What is claimed is:

1. A turbulator for promoting mixing of fluids passing through a body lumen in a patient comprising:

an elongate flow perturbing component including a proximal segment and a porous distal segment, the porous distal segment having a subordinate shape memory property and including an exposed wire coil with a fixed primary shape, a fixed secondary shape, and a mutable tertiary shape; and an elongate shape controlling component freely slidable within the flow perturbing component between a distally advanced location, and a retracted location, the elongate shape controlling component including a rigid proximal segment having a dominant shape memory property, and a non-rigid distal segment;

the elongate shape controlling component being positioned at the distally advanced location such that the turbulator is in a low profile, lumen access configuration at which the dominant shape memory property defines the mutable tertiary shape and the shape of the non-rigid distal segment is determined by the shape of the flow perturbing component; and the turbulator further being adjustable to an expanded profile, deployed configuration at which the subordinate shape memory property defines the mutable tertiary shape, at least in part by sliding the shape controlling component from the distally advanced location to the retracted location, to increase turbulence in the flow of a body fluid through the body lumen for mixing a treatment fluid therewith while flowing to a treatment site.

2. The turbulator of claim 1 wherein the flow perturbing component further includes a tubular fluid supply conduit extending between a fluid inlet located in the proximal segment and at least one fluid outlet located in the porous distal segment, the at least one fluid outlet being defined by a plurality of wire turns of the exposed wire coil.

3. The turbulator of claim 2 wherein the flow perturbing component includes a helical wire extending through each of the proximal segment and the distal segment thereof, the helical wire including the exposed wire coil and defining a longitudinal helix axis, and wherein the shape controlling component includes a non-helical wire positioned coaxially within the helical wire.

4. The turbulator of claim 3 wherein:
the fixed primary shape includes a circular cross sectional shape of the helical wire, and the fixed secondary shape includes a helical shape of the helical wire;
the fluid supply conduit defines a longitudinal passage axis collinear with the helix axis, in the lumen access configuration; and
the mutable tertiary shape includes a radially condensed shape of the exposed wire coil relative to the longitudinal passage axis, in the lumen access configuration.

5. The turbulator of claim 4 wherein the mutable tertiary shape includes a plurality of body turns of the helical wire about the longitudinal passage axis, in the deployed configuration.

6. The turbulator of claim 5 wherein the plurality of body turns includes each of a small radius turn and a large radius turn which are circumferential of the longitudinal passage axis.

7. The turbulator of claim 2 wherein the tubular fluid supply conduit includes a nonporous sheath extending from the fluid inlet to a proximal end of the exposed wire coil.

8. The turbulator of claim 7 wherein the nonporous sheath includes an external sheath attached to the helical wire.

* * * * *